United States Patent [19]

Snyckers et al.

[11] Patent Number: 4,752,606
[45] Date of Patent: Jun. 21, 1988

[54] PHARMACEUTICAL COMPOSITIONS AND PREPARATIONS THEREOF

[75] Inventors: Friedrich O. Snyckers; Theunis G. Fourie, both of Pretoria, South Africa

[73] Assignee: 501 Noristan Limited, South Africa

[21] Appl. No.: 650,574

[22] Filed: Sep. 14, 1984

Related U.S. Application Data

[63] Continuation of Ser. No. 485,728, Apr. 15, 1983, abandoned.

[30] Foreign Application Priority Data

Apr. 27, 1982 [ZA] South Africa ............... 82/2847

[51] Int. Cl.$^4$ ............... A61K 31/61; A61K 31/19
[52] U.S. Cl. ............... 514/163; 514/557; 514/974
[58] Field of Search ............... 514/163, 557

[56] References Cited

U.S. PATENT DOCUMENTS

| | | | |
|---|---|---|---|
| 3,070,623 | 12/1962 | Gottfried | 260/468.5 |
| 3,350,270 | 10/1967 | Gaunt | 424/157 |
| 3,436,454 | 4/1969 | Nouvel | 424/157 |
| 3,766,206 | 10/1973 | Hess | 260/309 |
| 3,859,328 | 1/1975 | Hess | 260/468.5 |
| 3,934,027 | 1/1976 | Hess | 424/309 |
| 3,944,660 | 3/1976 | Gottfried et al. | 424/157 |
| 4,154,833 | 5/1979 | Tauber et al. | 424/250 |
| 4,173,648 | 11/1979 | Pifferi et al. | 514/557 |
| 4,228,161 | 10/1980 | Shen | 514/420 |
| 4,378,354 | 3/1983 | Ghyczy et al. | 514/77 |

FOREIGN PATENT DOCUMENTS

| | | |
|---|---|---|
| 0009801 | 4/1980 | European Pat. Off. |
| 1205012 | 9/1970 | United Kingdom . |
| 1251976 | 11/1971 | United Kingdom . |
| 1251977 | 11/1971 | United Kingdom . |
| 1445831 | 8/1976 | United Kingdom . |
| 1493926 | 11/1977 | United Kingdom . |
| 1575494 | 9/1980 | United Kingdom . |
| 2075835 | 11/1981 | United Kingdom . |

OTHER PUBLICATIONS

Turner–*Screening Methods in Pharmacology*, (1965) p. 113 Academic Press, N.Y. & London.
Yamahara et al.–Yakugaku Zasshi, 95 (10), 1179–1182 (1975) English Translation.
Pharmacological Screening Report of "NL-62np" by Panlabs, Inc.
Kato, "Effects of a Stomachic Mixture on Gastric Secretion and Experimental Ulcerations in Rats", *Oyo Yakuri Pharmacometrics*, vol. 28, No. 5, 901 to 908, 1984.
Shibata, Proc. Asian Symp. Med. Plants Spices, vol. 1, pp. 59–70 (1981).

*Primary Examiner*—Frederick E. Waddell
*Attorney, Agent, or Firm*—Berman, Aisenberg & Platt

[57] ABSTRACT

The invention provides oleanolic acid and/or a physiologically acceptable salt thereof for use in treating a patient prophylactically and/or therapeutically for ulcerogenic-type disorders of the stomach and/or intestines. The ulcerogenic disorders can be of the type chemically induced and/or stress-induced.

The invention also provides a pharmaceutical composition comprising an active amount of oleanolic acid and/or a physiologically acceptable salt thereof in combination with an analgesic compound and/or an anti-inflammatory compound. The invention further provides for use of oleanolic acid in preventing and/or significantly reducing and/or therapeutically treating ulcerogenic-type disorders of the stomach and/or intestines.

12 Claims, No Drawings

PHARMACEUTICAL COMPOSITIONS AND PREPARATIONS THEREOF

This application is a continuation of Ser. No. 485,728, filed Apr. 15, 1983, now abandoned.

This invention relates to pharmaceutical compositions and preparations thereof. More particularly this invention relates to pharmaceutical compositions containing oleanolic acid and/or a physiologically acceptable salt thereof.

BACKGROUND OF THE INVENTION

Anti-ulcer properties have been reported for a number of compounds having the oleanane-type of triterpenoid structure. Amongst these compounds glycyrrhetinic acid(1)(3β-hydroxy-11-oxo-18β-olean-12-en-30-oic acid) esters, amides and salts thereof are particularly known for their usefull anti-ulcer activities and some of these compounds have also been used in the treatment of ulcers. One specific derivative of glycyrrhetinic acid that received widespread attention is carbenoxolone sodium (U.S. Pat. No. 3,070,623) which is the disodium salt of the hemisuccinate of glycyrrhetinic acid. It is reported to prevent the formation and to effect the healing of gastric ulcers in animals and humans. U.S. Pat. Nos. 3,766,206, 3,934,027 and 3,859,328 report 18β-glycyrrhetinic acid amides to be effective for the treatment of and for prevention of gastric and duodenal ulcers when administrered orally or intraperitoneally. In Belgian Pat. No. 628,444 the anti-ulcer properties of a number of metal salts of glycyrrhetinic acid and its hemi-esters are reported. In European Pat. No. 0,009,801 (18β and 18α)-2α-cyano-3,11-dioxo-olean-12-en-29-oic acid and lower alkyl derivatives thereof are reported to be effective in the treatment and/or prevention of gastric and duodenal ulcers when administered orally.

Glycyrrhizinic acid, the β,β'-glucoronic acid ester of glycyrrhetinic acid, is present in liquorice, which is known to be effective in the treatment of gastric and duodenal ulcers. In British Pat. No. 1,445,831 it is claimed that the aluminium or iron salts of glycyrrhizinic acid are effective anti-ulcer compounds with hardly any or none of the undesirable side effects known for the parent acid.

Derivatives of ursolic acid are also known to possess anti-ulcer properties. In British Pat. No. 1,251,977, for instance, the preparation and anti-ulcer properties of esters of ursolic acid of the type 2 (R and R' not equal to hydrogen) are described.

In British Pat. No. 1,205,012 the isolation of liquiritic acid (3) from and extract of Glycyrrhiza glabra is described. Liquiritic acid, which is a stereo-isomer of glycyrrhetinic acid (1), has been found to possess cicatrisant, anti-inflammatory and anti-ulcer properties.

Derivatives of oleanolic acid (oleanolic acid: 4, R and R'=H) have also been acclaimed for their anti-ulcer properties. In British Pat. No. 1,251,976 esters of the type 4

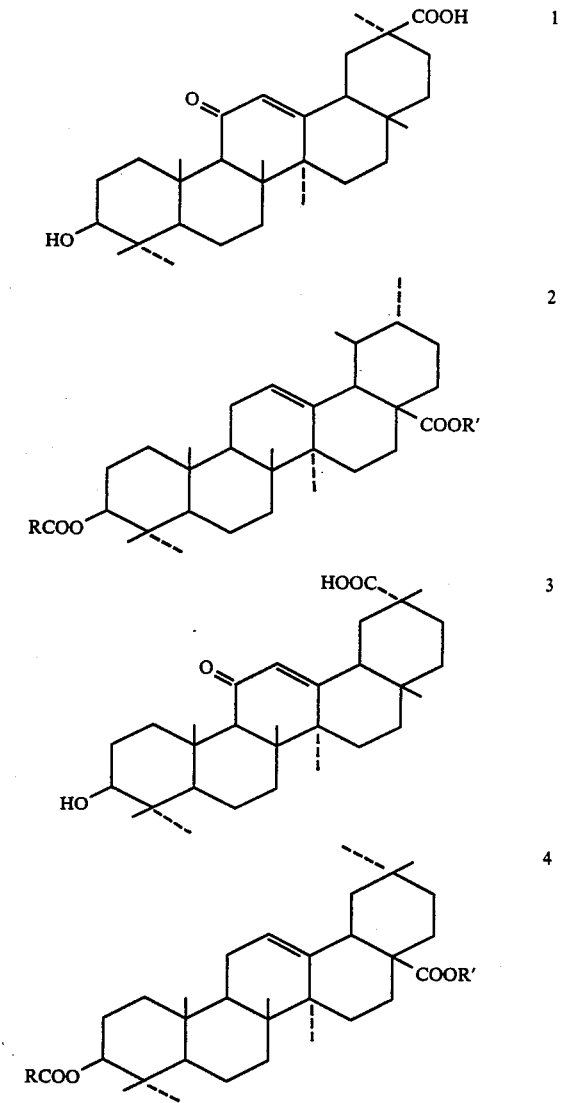

(with R and R' not equal to hydrogen) of oleanolic acid are reported to be active anti-ulcer compounds. In Example 10 of the latter patent the glucose induced anti-ulcer activity of three of the esters and oleanolic acid are given. Oleanolic acid was included in this test apparently for purposes of reference or comparison.

While the three esters showed marked reduction (21 to 60%) in ulceration, a non-significant reduction of 8% in ulceration was observed for oleanolic acid. This test suggests that the chemically induced ulceration is not significantly reduced by oral administration of oleanolic acid. In another report the anti-ulcer activities of glycyrrhetinic acid and related compounds, including oleanolic acid, were evaluated (S. Shibata in Proc. Asian Symp. Med. Plants Spices, K. Kusamran (Ed), vol. 1, pp. 59–78, 1981). Firstly, the inhibiting activities against stress-induced ulceration in mice are given (p. 65). Two of the test compounds (glycyrrhetinic acid and olean-12-en-3β, 30-diol) were reported to exhibit promising inhibiting activity. By contrast, the results obtained in the latter test suggest non-significant, if any, inhibiting activity against stress-induced ulceration for oleanolic acid. The paper also describes (p. 66) the effect of the glycyrrhetinic acid type of compounds against aspirin-induced ulceration, but only two compounds (glycyrrhetinic acid and olean-12-en-3β, 30-diol) which showed positive reduction of the stress-induced ulceration, were included.

It is therefore seen that although oleanolic acid has been included in tests together with other oleanane-type of triterpenoid compounds, the results reported showed no substantial, if any, preventative effect for oleanolic acid against stress-induced and chemically-induced ulceration.

The inescapable conclusion from the prior art data is therefore that oleanolic acid is not suitable for the prevention of stress-induced and chemically-induced ulceration. Furthermore, no mention can be found in the prior apt of any healing effects of oleanolic acid in respect of ulcers.

SUMMARY OF THE INVENTION

Surprisingly, therefore, it has now been found by the present applications that oleanolic acid (or salts thereof) is effective for the prevention and the healing of ulcers.

It has been found that chemically induced ulceration, i.e. produced by analgesic and/or anti-inflammatory drugs, such as aspirin and indomethacin, or other chemical agents, is significantly reduced when these drugs are administered in conjunction with oleanolic acid (or the aforesaid salts). Furthermore, it has been found that the toxicity of the organic acids, e.g. salicylic acid and other analgesic and/or anti-inflammatory drugs is reduced to a significant extent when administered in conjunction with oleanolic acid. The fact that the intrinsic beneficial activity of the analgesic and/or anti-inflammatory drugs is not detrimentally influenced by their use in conjunction with oleanolic acid, very much enhances the value of this invention. It has also been found that oleanolic acid itself possesses some analgesic activity and also that the combined use of oleanolic acid (or its aforesaid salts) with analgesic drugs results in an additive analgesic effect.

It has furthermore been found that pharmaceutical preparations comprising oleanolic acid or the salts thereof are also significantly effective in the prevention or reduction of stress induced gastro-intestinal ulcerations.

It has furthermore been found that oleanolic acid (or its aforesaid salts) is also effective in the healing of ulcers. It will also be understood that whenever oleanolic acid is used for the treatment of ulcers the aforesaid analgesic activity of oleanolic acid may in addition be beneficial in relieving the pain associated with ulcers.

The acute toxicity of oleanolic acid, which is present in edible fruit, such as grapes, is very low. Toxic doses are considerably higher than the therapeutic doses contemplated in accordance with the present invention.

Also in accordance with the present invention there are provided pharmaceutical compositions comprising an effective amount of oleanolic acid and/or a physiologically acceptable salt thereof optionally in combination with a pharmaceutical diluent or adjuvant.

Further in accordance with the present invention, there are provided pharmaceutical compositions comprising an effective amount of oleanolic acid and/or a physiologically acceptable salt thereof in combination with one or more analgesic and/or anti-inflammatory compound(s) in an effective and tolerated amount and concentration.

Further in accordance with the present invention there are provided pharmaceutical compositions comprising an effective amount of oleanolic acid and/or a physiologically acceptable salt thereof in combination with one or more compatible compound(s) effective in the treatment of stress conditions.

It is therefore feasible that such compositions can be usefully employed for the healing of ulcers, and to reduce the formation of gastro-intestinal ulcers whether chemically or stress-induced.

The analgesic and/or anti-inflammatory compounds or drugs contemplated may include the following substances:

Aspirin and aspirin derivatives, such as benorylate; salicylic acid, salicylates and derivatives, such as flufenisal; indoleacetic acids, such as indomethacin; phenylacetic acids such as ibuprofen; N-arylanthranilic acids, such as mefenamic acid; and any other acidic or other substances used in the treatment of pain and inflammatory conditions which substances cause or promote gastro-intestinal damage.

Physiologically acceptable salts of oleanolic acid which may be employed may include one or more of the following:

Sodium oleanolate;
Ammonium oleanolate;
Calcium oleanolate;
Magnesium oleanolate;
Aluminum oleanolate; or the like.

Further in accordance with the present invention there are provided pharmaceutical formulations of oral dosage forms comprising an effective amount of oleanolic acid and/or a physiologically acceptable salt thereof for release of the active ingredient at a desired site in the gastro-intestinal tract, for instance either in the stomach and/or duodenum according to known formulation techniques, e.g. slow releasing tablets.

Still further in accordance with the invention, there are provided pharmaceutical compositions comprising an effective tolerated amount of oleanolic acid and/or a physiologically acceptable salt thereof and a known compound effective in preventing ulcer formation and/or a known compound effective in thereapeutically treating ulcers and/or a known compound(s) effective in relieving the symptoms associated with ulcers, such as an antacid, e.g. aluminum hydroxide.

Due to its low toxicity, high dosages of oleanolic acid or salts thereof, can therefore be employed to produce useful results, depending upon the particular effect which is required.

Oleanolic acid is particularly suitable for oral administration and for that reason the preparations of oleanolic acid, or salts thereof, are preferably of a kind intended for oral use, namely: tablets, coated tablets, dragees, capsules, powders, granulates and soluble tablets, and liquid forms, e.g. suspensions, dispersions or solutions, optionally together with an additional active ingredient, such as one or more analgesic and/or anti-inflammatory compound(s), as discussed above.

The invention extends to a method of preparing such pharmaceutical compositions as described hereinbefore and compositions when so prepared. The compositions may be manufactured by a method which comprises mixing oleanolic acid and/or a salt thereof as above defined with a pharmaceutically acceptable carrier or auxiliary, and optionally with an analgesic and/or anti-inflammatory substance and/or another compound(s) as aforesaid.

Oleanolic acid is a known compound occurring naturally in plants, and may be prepared by any of the extraction methods known in the art.

The salts of oleanolic acid may be prepared according to methods known in the art of preparation of salts of lipophylic carboxylic acids. Alternatively, the salts of oleanolic acid can be prepared directly from plant material containing oleanolic acid in any known manner. The salts of oleanolic acid may be purified by methods known in the art, preferably by, recrystallisation from aqueous organic solvents such as aqueous alcohols.

According to a still further feature of the present invention, there is provided a method of treatment of patients suffering from, or susceptible to, ulcerogenic type disorders of the stomach and intestines, particularly acute and chronic gastric and duodenal ulcers and related conditions, which comprise administering to the said patient an effective amount of oleanolic acid and/or a physiologically acceptable salt thereof, optionally together with additional active ingredients as discussed above.

DETAILED DESCRIPTION OF THE INVENTION

The invention and its various aspects will now be described hereunder. Examples 1 and 2 are not to be regarded as part of the invention but are intended rather for information and background.

EXAMPLE 1

Preparation of Oleanolic Acid

Suitable plant material, for example grape husks (preferably dried and milled), is exhaustively extracted with such solvents in which oleanolic acid is soluble.

These include:

aromatic solvents, such as benzene;
esters, such as ethyl acetate;
ketones, such as acetone;
halogenated hydrocarbons, such as chloroform and dichloromethane;
alcohols, such as methanol and ethanol;
ethers, such as diethyl ether or dioxane;
and mixtures thereof.

Preferably the extractions are performed with chloroform, dichloromethane, ethanol, or methanol, or mixtures thereof.

From these extracts, the oleanolic acid can be separated by any method known in the art.

Preferably the extracts are treated with sufficient aqueous base to effect conversion into a water soluble salt of oleanolic acid. Preferably a diluted sodium hydroxide solution is used for this purpose.

The aqueous solution of this salt is now treated with a suitable water immiscible solvent (such as dichloromethane or diethyl ether) to remove the bulk of the non-acidic components from the aqueous phase.

The purified aqueous solution containing the salt of oleanolic acid is now acidified with a suitable acid (preferably hydrochloric or sulphuric acid), to reconvert the salt to oleanolic acid.

The crude oleanolic acid can now be recovered by filtration or sedimentation, but preferably by extraction with a solvent which is not water miscible but which is a good solvent for oleanolic acid (preferably dichloromethane or diethyl ether), and subsequent evaporation of that extract.

Purification of the crude oleanolic acid can be achieved by recrystallisation or chromatography.

EXAMPLE 2

Preparation of Sodium Oleanolate

A 10% aqueous solution of sodium hydroxide is added to an almost saturated solution of oleanolic acid in a water immiscible solvent, for example dichloromethane or diethyl ether. The volume of the sodium hydroxide solution is controlled by the amount of oleanolic acid taken; the final mixture should contain at least one, preferably 1,5 to 3, mole sodium hydroxide per mole oleanolic acid—a large excess of the sodium hydroxide solution may lower the yield. The mixture is mixed well (vigorous stirring or shaking) and the precipitated sodium oleanolate is separated. The sodium oleanolate can be recrystallised from aqueous organic solvents, preferably aqueous methanol or aqueous ethanol.

PHARMACOLOGICAL TESTS

Test 1

Analgesic Activity of Oleanolic Acid

The analgesic effect of the compound was tested in oral application to rats. 45 Minutes after application of the compound, the rats received an intraperitoneal injection of 1.0 ml 1% acetic acid. This causes a series of characteristic spasms in the untreated control animals. Analgesic effects are indicated by the reduction of the frequency of these spasms. The following results were obtained with the compound:

| Dose (mg/kg) | Average No. of spasms (25 mins) | % Inhibition |
| --- | --- | --- |
| Untreated (control) | 43.75 | — |
| 10 | 40.0 | 8.6 |
| 31.6 | 22.12 | 49.4 |
| 100 | 15.10 | 65.7 |

Test 2

Activity of Oleanolic Acid against Stress Induced Ulcers

Stress induced ulcers are experimentally caused in rats by encasing the animals in plaster of Paris bandages for 24 hours. The effect of compounds on this formation of stress ulcers is assessed by applying the drugs 1 hour before encasing the animals in the bandage and again 6 hours after encasing the animals. After 24 hours, the bandage is removed and gastric damage is assessed compared to that of untreated animals.

Treating the animals with the compound at a dose of 100 mg/kg resulted in an 83.5% inhibition of the mean total ulceration score.

Test 3

Influence of Oleanolic Acid and Sodium Oleanolate on Gastric damage caused by Administration of Analgesic/Anti-Inflammatory Drugs in Rats Gastric damage caused by irritant substances (e.g. aspirin, indomethacin or other acidic analgesic/anti-inflammatory drugs) is assessed by applying a suitable dose of the protective compound followed later by a relatively high dose of the irritant (in the case of aspirin, approximately 550 mg/kg). After a further 5 hours, the extent of gastric damage is determined.

A. Effect on gastric damage cuased by Aspirin

Dose related reductions of the gastric damage were found as follows:

| (i) Dose of oleanolic acid (mg/kg) | Percentage inhibition of Aspirin induced gastric damage |
|---|---|
| 30 | 28 |
| 100 | 49 |
| 300 | 69 |

| (ii) Dose of sodium oleanolate (mg/kg) | Percentage inhibition of Aspirin induced gastric damage |
|---|---|
| 30 | 1 |
| 100 | 30 |
| 300 | 47 |

B. Effect on Gastric Damage Caused by Indomethacin

A dose related inhibition of the gastric damage was found as follows:

| Dose of oleanolic acid (mg/kg) | Percentage inhibition of Indomethacin induced gastric damage |
|---|---|
| 10 | 61 |
| 30 | 66 |
| 100 | 80 |
| 300 | 86 |

Test 4

Acute toxicity of Oleanolic Acid

The low acute toxicity of oleanolic acid is illustrated by the fact that doses up to 4000 mg/kg did not cause any deaths in mice when administered by oral route.

Test 5

Influence of Oleanolic Acid on Gastric Damage caused by Administration of Resperine in Rats The animals were treated with oleanolic acid (per os; tragacanth vehicle) and directly thereafter with reserpine (6 mg/kg; subcutaneous injection). After 16 hours the extent of gastic damage was determined.

Treating the animals with oleanolic acid at a dose of 100 mg/kg resulted in a 25% inhibition of reserpine induced gastric damage compared with an untreated control group.

Test 6

Influence of Oleanolic Acid on Gastric damage (HCl - Gastrin ulcer) caused by Administration of Tetragastrin in Rats Each animal was treated with hydrochloric acid (0,2 ml of a 20% solution; per os) on day zero. From day one onwards to day 14 the animals were treated once daily with tetragastrin (100 µg/kg/day; intraperitoneal injection) and twice daily with the protective compound (100 mg/kg/treatment; per os in tragacanth). On day 15 the extent of gastric damage was determined.

In this test oleanolic acid brought about 49% inhibition of gastric damage and cimetidine a 41% reduction of gastric damage compared with an untreated control group.

Test 7

Healing effect of Oleanolic Acid on thermally Induced Ulceration in Rats

Thermal stomach ulceration was induced on day zero by means of a heated (75° C.) stainless steel stamp (5 mm in diameter). From day one onwards to day 13 the animals were treated twice daily with oleanolic acid (100 mg/kg; per os in tragacanth). On day 14 the animals were examined for the extent of gastric damage.

Oleanolic acid brought about a 59% reduction of gastric damage in this test compared with an untreated control group.

Test 8

Healing effect of Oleanolic Acid on chemically Induced Ulceration in Rats

Ulceration was induced by injecting 30% acetic acid into the stomach of the animals on day zero. From day one onwards to day 10 the animals were treated twice daily with the protective compound (100 mg/kg; per os). On day 11 the extent of gastric damage was determined.

Treating the animals with oleanolic acid resulted in a 73% reduction of gastric damage, compared with an untreated control group, while carbenoxolone sodium gave a 42% reduction in the same test.

Test 9

Reduction of Acute Toxicity of Aspirin when administered in Conjunction with Oleanolic Acid Oral administration of aspirin and of a mixture of aspirin and oleanolic acid (in a 1:1 mass ratio) to mice gave the following results:

| Treatment | LD 50 (mg/kg) | | |
|---|---|---|---|
| | Males | Females | Combined |
| Aspirin alone | 1110 | 2100 | 1800 |
| Aspirin and oleanolic acid | Greater than 4100 in all cases | | |

Test 10

Lack of Interference of Oleanolic Acid with the anti-Inflammatory effect of Aspirin The lack of interference of oleanolic acid with the anti-inflammatory effect of aspirin was demonstrated by comparing the inhibition of swelling (in a carrageenan induced rat paw oedema) by aspirin alone to that of aspirin at the same dose in the presence of various quantities of oleanolic acid. The compounds (aspirin and oleanolic acid) were administered orally.

| Dose of oleanolic acid (mg/kg) | Dose of Aspirin (mg/kg) | % inhibition at time (hrs) geenan injection | | | |
|---|---|---|---|---|---|
| | | 1.5 | 3 | 4.5 | 6 |
| — | 25 | 12 | 17 | 11 | 18 |
| — | 50 | 18 | 32 | 17 | 16 |
| — | 100 | 30 | 42 | 32 | 23 |
| — | 200 | 45 | 52 | 34 | 30 |
| 25 | 25 | 23 | 19 | 22 | 6 |
| 50 | 50 | 25 | 23 | 13 | 14 |
| 100 | 100 | 33 | 40 | 32 | 22 |
| 200 | 200 | 44 | 36 | 29 | 25 |

The differences recorded in the above test between aspirin alone and aspirin plus oleanolic acid are not significant, illustrating the lack of significant interference by oleanolic acid.

Test 11 The analgesic effect of Aspirin in the presence of Oleanolic Acid

Measurement of the analgesic effect of the test compounds was done as set out in Test 1. The $ED_{50}$ was computed for the various treatments as follows:

| Treatment | ED50 (mg/kg) |
| --- | --- |
| Aspirin | 22.3 |
| Oleanolic Acid | 55.8 |
| Aspirin & oleanolic acid (mass ratio 1:1) | 16.0 (expressed in terms of aspirin) |

These figures illustrate that not only does oleanolic acid not inhibit the analgesic effect of aspirin but in fact that there is an additive analgesic effect apparently due to the intrinsic analgesic activity of oleanolic acid.

Test 12

The antithrombotic effect of Aspirin in the presence of Oleanolic Acid

Aspirin inhibits the occurrence of pulmonary thrombo-embolism in animals treated with arachnidoic acid. Oleanolic acid has no effect in this regard. Addition of oleanolic acid to aspirin in a mass ratio of 1:1 causes a non-significant change in $ED_{50}$ (expressed in terms of aspirin) from 41 mg/kg for aspirin alone to 48 mg/kg for the mixture. This shows that oleanolic acid does not significantly inhibit the antithrombotic effect of aspirin.

PREPARATION OF PHARMACEUTICAL COMPOSITIONS

Oleanolic acid or one of its salts may be incorporated in pharmaceutical compositions for administration to a patient. The method of preparing such compositions includes the steps of ensuring that the compound(s) are free of undesirable impurities—this may require repeated recrystallisation or washing; comminuting the compound(s) to a required particle size; and incorporating the compound(s) for example oleanolic acid either alone or in combination with at least one analgesic and/or anti-inflammatory drug or other compound mentioned above, for example aspirin, into a desired form for administration to a patient, for example in a solid (powder, tablet or capsule form with a pharmaceutically-acceptable carrier or adjuvant) or in a liquid form (suspension or solution) for oral ingestion.

The method may include treating the compound(s) or composition(s) to any other step(s) conventionally applied in preparing pharmaceutical compositions.

EXAMPLE OF FORMULATION OF TABLETS

Tablets, each weighing 500mg and containing 100 mg of oleanolic acid were manufactured as follows:

| Composition (for 10 000 tablets) | |
| --- | --- |
| Oleanolic acid | 500 g |
| Avicel PH102 | 1700 g |
| Kollidon CL | 6.25 g |
| Aerosil Plain 200 | 25 g |
| Dried Starch (maize) | 25 g |

| Composition (for 10 000 tablets) | |
| --- | --- |
| Magnesium Stearate | 187.5 g |

PROCEDURE

Oleanolic acid, Avicel PH102 and Kollidon CL were mixed and the mixture was then forced through a sieve of 0.5 mm openings. Aerosil Plain 200 and dried maize starch were mixed and the mixture forced through a sieve of 0.3 mm openings. The two sieved mixtures and magnesium stearate of partical size less than 0.3 mm were combined and mixed well. The total mixture was then granulated by means of mechanical granulation. The granules were finally processed into tablets using punches of 13 mm diameter.

We claim:

1. A method of preventing, significantly reducing or therapeutically treating an ulcerogenic-type disorder which comprises:
   administering an effective amount of oleanolic acid and/or a physiologically-acceptable salt thereof to a patient susceptible to or afflicted with such a disorder and
   administering to the patient an amount of aspirin which, in the absence of the oleanolic acid and/or salt thereof, would produce an unacceptable level of acute toxicity, and
   wherein the amount of oleanolic acid and/or salt thereof is sufficient to reduce the acute toxicity to an acceptable level.

2. A method of producing both an analgesic and an anti-ulcerogenic effect in a mammal in need of such therapy which comprises:
   administering to the mammal an amount of oleanolic acid and/or a physiologically-acceptable salt thereof which is sufficient to produce both the analgesic and anti-ulcerogenic effect and
   substantially contemporaneously administering to the mammal an analgesic amount of salicylic acid and/or a derivative thereof which, in the absence of the oleanolic acid and/or salt thereof, would induce an undesirable level of acute toxicity in said mammal;
   the amount of oleanolic acid and/or salt thereof being sufficient to reduce the level of acute toxicity to an acceptable level.

3. A method of producing an analgesic effect in a mammal in need of such treatment which comprises:
   administering to the mammal an effective amount of oleanolic acid and/or a physiologically-acceptable salt thereof, and
   administering to said mammal an amount of a substance which causes or promotes gastrointestinal damage in the absence of oleanolic acid and/or salt thereof, the substance and the amount being effective to alleviate pain or an inflammatory condition;
   the amount of oleanolic acid and/or salt thereof being sufficient to counteract the cause or promotion of such gastrointestinal damage.

4. A method of producing an analgesic effect in a mammal in need of such treatment which comprises:
   administering to the mammal an effective amount of oleanolic acid and/or a physiologically-acceptable salt thereof, and administering to said mammal an amount of aspirin which, in the absence of the oleanolic acid and/or the physiologically-acceptable salt thereof, would produce an unacceptable level of acute toxicity, and wherein the amount of oleanolic acid and/or the salt thereof is sufficient to reduce the acute toxicity to an acceptable level.

5. A method of producing an analgesic effect and preventing, significantly reducing or therapeutically treating an ulcerogenic-type disorder which comprises:
administering an effective amount of oleanolic acid and/or a physiologically-acceptable salt thereof to a patient in need of an analgesic and susceptible to or afflicted with such a disorder and
administering to the patient an amount of aspirin which, in the absence of the oleanolic acid and/or the physiologically-acceptable salt thereof, would produce an unacceptable level of acute toxicity;
the amount of oleanolic acid and/or the salt thereof being sufficient to reduce the acute toxicity to an acceptable level.

6. A method according to claim 1 wherein the disorder is chemically-induced ulceration.

7. A method according to claim 1 wherein the disorder is stress-induced ulceration.

8. A method of preventing or treating an ulcerogenic disorder in a human or other animal host and simultaneously reducing acute toxicity of aspirin, an aspirin derivative, salicylic acid, a salicylate or a salicylate derivative administered to the host, which method comprises administering an effective amount of oleanolic acid to said host.

9. In a method which comprises administering to a mammal in need of such therapy an effective amount of a substance for alleviating pain or an inflammatory condition, the substance being one which causes or promotes gastro-intestinal damage, the improvement which comprises administering to the mammal an amount of oleanolic acid and/or a salt thereof sufficient to counteract the cause or promotion of such gastro-intestinal damage.

10. In a method which comprises administering an analgesic amount of salicylic acid and/or a derivative thereof to a mammal in need to such treatment and wherein the amount is sufficient to result in an undesirable level of acute toxicity, the improvement which comprises administering to the mammal a sufficient amount of oleanolic acid and/or a physiologically-acceptable salt thereof to reduce the acute toxicity to an acceptable level.

11. A method according to claim 5 wherein the ulcerogenic-type disorder is stress-induced ulceration.

12. A method according to claim 5 wherein the ulcerogenic-type disorder is chemically-induced ulceration.

* * * * *